United States Patent
Forrester

(10) Patent No.: US 8,078,040 B2
(45) Date of Patent: Dec. 13, 2011

(54) HEATABLE HOSE

(75) Inventor: Martin Forrester, Trenton (CA)

(73) Assignee: Schauenburg Hose Technology GmbH, Muelheim an der Ruhr (DE)

( * ) Notice: Subject to any disclaimer, the term of this patent is extended or adjusted under 35 U.S.C. 154(b) by 326 days.

(21) Appl. No.: 12/417,886

(22) Filed: Apr. 3, 2009

(65) Prior Publication Data

US 2010/0215351 A1    Aug. 26, 2010

(30) Foreign Application Priority Data

Feb. 20, 2009  (DE) .................. 10 2009 009 790

(51) Int. Cl.
*F24H 1/10* (2006.01)
(52) U.S. Cl. ...................................... 392/481
(58) Field of Classification Search ........... 392/465–496
See application file for complete search history.

(56) References Cited

U.S. PATENT DOCUMENTS

| | | | |
|---|---|---|---|
| 2,739,616 A | 3/1956 | Duff | |
| 3,674,056 A | 7/1972 | D'Aprile | 138/134 |
| 3,739,815 A | 6/1973 | Rejeski | 138/122 |
| 3,861,424 A | 1/1975 | Mizutani et al. | 138/119 |
| 3,910,808 A | 10/1975 | Steward | 156/429 |
| 3,962,019 A | 6/1976 | Rejeski | 156/428 |
| 3,963,856 A | 6/1976 | Carlson et al. | 174/47 |
| 3,966,525 A | 6/1976 | Steward | 156/195 |
| 4,038,519 A | 7/1977 | Foucras | 219/301 |
| 4,043,856 A | 8/1977 | Steward | 156/195 |
| 4,063,067 A * | 12/1977 | Bouffenie et al. | 392/473 |
| 4,098,298 A | 7/1978 | Vohrer | 138/122 |
| 4,294,636 A | 10/1981 | Vitellaro | 156/143 |
| 4,304,266 A | 12/1981 | Kutnyak et al. | 138/129 |
| 4,337,800 A | 7/1982 | Carlson et al. | 138/122 |
| 4,375,381 A | 3/1983 | Carlson et al. | 156/195 |
| 4,383,555 A | 5/1983 | Finley | 138/129 |
| 4,477,715 A * | 10/1984 | Bell et al. | 219/205 |
| 4,489,759 A | 12/1984 | Yamamura | 138/122 |
| 4,587,145 A | 5/1986 | Kanao | 428/36 |
| 4,599,784 A | 7/1986 | Canu, Jr. et al. | 29/450 |
| 4,686,354 A | 8/1987 | Makin | 219/301 |
| 4,714,508 A | 12/1987 | Chivens et al. | 156/195 |
| 4,780,261 A | 10/1988 | Vajtay | 264/285 |
| 4,823,767 A * | 4/1989 | Wust | 126/20 |
| 4,826,423 A | 5/1989 | Kemp et al. | 425/505 |
| 4,866,250 A * | 9/1989 | Pasbrig | 392/479 |
| 5,357,948 A | 10/1994 | Eilentropp | 128/204.17 |

(Continued)

FOREIGN PATENT DOCUMENTS

DE      33 12 434 A1      4/1983

(Continued)

*Primary Examiner* — Daniel L Robinson
(74) *Attorney, Agent, or Firm* — David A. Burge

(57) ABSTRACT

A heatable hose (1), in particular a respiration hose, having a flexible hose wall (4), shall guarantee through its design that a contact of the electric conductors or heating wires (14, 16) accommodated in the hose (1) and, thus, a short circuit, is excluded. For this purpose, the hose (1) is equipped with a plurality of reinforcing ribs (8, 12, 20, 22), each of which winds around the hose wall (4) in the manner of a helical line and which form together a multiple-threaded helical line, at least two reinforcing ribs (8, 12) being provided, each of which encloses a heating wire (14, 16) designed for heating the hose. Each heating wire (14, 16) is preferably a single-conductor wire.

19 Claims, 4 Drawing Sheets

U.S. PATENT DOCUMENTS

| | | | |
|---|---|---|---|
| 5,394,507 A * | 2/1995 | Okamoto | 392/480 |
| 5,454,061 A | 9/1995 | Carlson | 392/478 |
| 5,537,996 A | 7/1996 | McPhee | 128/204.17 |
| 5,555,915 A | 9/1996 | Kanao | 138/133 |
| 5,637,168 A | 6/1997 | Carlson | |
| 5,848,223 A | 12/1998 | Carlson | 392/478 |
| 6,024,132 A | 2/2000 | Fujimoto | 138/122 |
| 6,152,186 A | 11/2000 | Arney et al. | 138/129 |
| 6,190,480 B1 | 2/2001 | Carlson | 156/143 |
| 6,219,490 B1 | 4/2001 | Gibertoni et al. | 392/472 |
| 6,305,428 B1 | 10/2001 | Nakamura et al. | 138/126 |
| 6,347,646 B2 | 2/2002 | Fukui et al. | 138/129 |
| 6,367,510 B1 | 4/2002 | Carlson | |
| 6,394,143 B1 | 5/2002 | Diels et al. | 138/121 |
| 6,659,136 B2 | 12/2003 | Fukui et al. | 138/125 |
| 6,827,109 B2 | 12/2004 | McCaughtry | 138/134 |
| 6,948,527 B2 | 9/2005 | Ragner et al. | 138/119 |
| 7,156,127 B2 | 1/2007 | Moulton et al. | 138/122 |
| 7,431,054 B2 | 10/2008 | Kramer, Jr. et al. | 138/133 |
| 7,468,116 B2 | 12/2008 | Smith et al. | 156/344 |
| 7,520,302 B2 | 4/2009 | Smith | 138/118 |
| 7,597,119 B2 | 10/2009 | Boettner | 138/119 |
| 2003/0098084 A1 | 5/2003 | Ragner et al. | 138/129 |
| 2006/0165829 A1 | 7/2006 | Smith et al. | 425/113 |
| 2008/0035229 A1 | 2/2008 | Kramer et al. | 138/132 |
| 2009/0050227 A1 | 2/2009 | Smith | 138/122 |
| 2009/0277525 A1 | 11/2009 | Jourdan | 138/122 |
| 2010/0224276 A1 | 9/2010 | Forrester et al. | 138/122 |

FOREIGN PATENT DOCUMENTS

| | | |
|---|---|---|
| DE | 84 26 279 U1 | 9/1984 |
| DE | 38 35 248 A1 | 10/1988 |
| DE | 40 39 215 A1 | 12/1990 |
| DE | 4039215 A1 | 6/1992 |
| DE | 295 07 806 U2 | 5/1995 |
| DE | 695 27 528 T2 | 5/1995 |
| DE | 197 52 008 A1 | 11/1997 |
| DE | 199 04 864 A1 | 2/1999 |
| DE | 20 2005 013786 | 12/2005 |
| DE | 10 2009 009790 | 2/2009 |
| EP | 0097901 | 6/1983 |
| EP | 0201985 | 2/1986 |
| EP | 0742399 | 5/1996 |
| EP | 0917851 | 11/1997 |
| EP | 1181945 | 2/2002 |
| EP | 1181945 A1 | 2/2002 |
| WO | WO 95/33163 | 5/1995 |
| WO | WO 2004/011072 | 7/2003 |
| WO | WO 2004/024429 | 11/2003 |
| WO | WO 2006/094576 | 1/2006 |
| WO | 2006094576 A1 | 9/2006 |

* cited by examiner

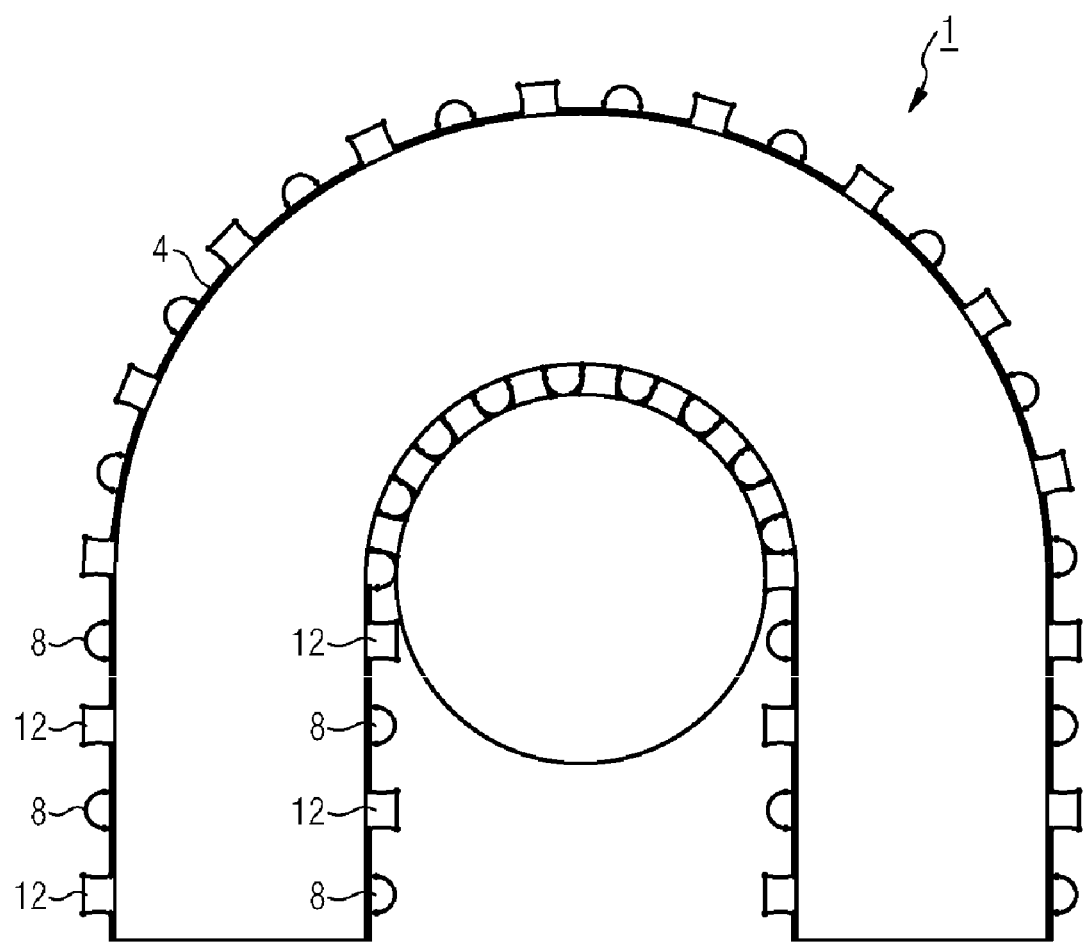

HEATABLE HOSE

FIELD OF THE INVENTION

The invention relates to a heatable hose, in particular a respiration hose, having a flexible hose wall.

BACKGROUND OF THE INVENTION

Heatable hoses with flexible hose walls are widely used. They are mainly applied as respiration hoses, for example for medical purposes or for pulmonary automatic devices for diving or for rescue purposes. The hoses are manufactured with as thin a hose wall as possible, in order to be as flexible and lightweight as possible. Respiration hoses are, as a rule, heatable, to prevent condensation of the humidity accumulating in the hose. The presence of humidity in a respiration hose is inevitable if the respiration air supplied to a patient has to be humidified. Excessive condensed humidity in the respiration hose may lead to both hygienic and technical problems. In particular, during respiration, no water must get into the patient's lungs. If the heating of the hose and, thus, the heating temperature is controlled by temperature-measuring arrangements inside the hose, these measured values may be adulterated through the presence of (water) condensate. To completely avoid the condensation of humidity, as uniform a heating as possible over the entire length of the hose is desirable.

Different embodiments of heatable hoses are known, in which the hose is usually heated by means of heating wires (resistance wires). The heating wires can be arranged both inside and outside the hose wall. The hose wall can be surrounded, for example, by a helicoidal outer support bead, also called "reinforcing rib", a pair of electric conductors or a pair of heating wires being carried in the support bead or between support bead and hose wall. The two heating wires can be connected with each other on one end of the hose in an electrically conductive manner, to bring about a closed heating-current circuit, while the other two ends of the heating wires are led out of the support bead on the other end of the hose and can be connected to the poles of a voltage source or a heating-current source. The current flowing in this way through the heating wires heats the heating wires, which, in turn, heat the hose and the medium flowing therein. Such a hose is known, for example, from DE 695 27 528 T2.

Due to the spatial proximity of the heating wires arranged in the helicoidal support bead or the reinforcing spiral, a contact of the two electric conductors or heating wires and, thus, a short circuit might occur. As the reinforcing spiral strengthening the hose wall has to guarantee a high flexibility of the hose, a suitable dimensioning of the reinforcing spiral results, of course, in spatial proximity of the two heating wires.

SUMMARY OF THE INVENTION

Therefore, the invention is based on the task to provide a flexible, electrically heatable hose the construction of which guarantees that a contact of the accommodated electric conductors or heating wires and, thus, a short circuit, is excluded.

This task is solved according to the invention by a plurality of reinforcing ribs winding around the hose wall in the manner of a helical line and forming together a multi-threaded helical line, at least two reinforcing ribs being provided, each of which encloses a heating wire designed for heating the hose. Each heating wire is preferably designed as a single-conductor wire.

Advantageous embodiments of the invention are the subject matter of the dependent claims.

The invention is based on the consideration that a contact of the electric conductors or heating wires and a resulting short circuit can consistently be avoided if the heating wires are both electrically insulated and spatially separated from each other. Such an insulation and spatial separation of the heating wires can be achieved by the fact that the hose is helicoidally enclosed by two reinforcing ribs, each helicoidal reinforcing rib accommodating only one single-conductor heating wire.

In a preferred embodiment, exactly two reinforcing ribs are provided, each reinforcing rib accommodating exactly one single-conductor heating wire. The two reinforcing ribs wind around the hose wall in the form of a two-threaded helical line or double helix. The heating wire can be embedded in the respective reinforcing rib or be located between hose wall and reinforcing rib. The reinforcing ribs can be formed onto the hose wall or be connected with the hose wall in a suitable manner, for example by bonding or gluing. The reinforcing ribs can also be completely integrated in the hose wall and enveloped by the latter. Hose wall and reinforcing ribs can be made of different materials or of the same material, possibly in one operation.

On the other hand, such a construction should not impair the flexibility of the hose. It has been found out that this can be achieved by manufacturing the respective spiral with a higher lead than those usual up to now. That means that, as compared with a conventional hose with only one reinforcing spiral, the two reinforcing ribs can be manufactured with higher leads, with identical flexibility of the hose. Viewed in longitudinal direction of the hose, the length of one thread of one of the two reinforcing spirals or reinforcing ribs can be, for example, for a hose according to the invention, twice as long as in the conventional embodiment with only one reinforcing spiral. This reduces the length of the heating wires embedded in the reinforcing spirals, so that material can be saved. Nevertheless, the two spatially separated heating wires guarantee a uniform heating of the hose on all sides.

Depending on the application of the hose, it is advantageous to equip or connect the hose with measuring units or open-loop and/or closed-loop control units. For this purpose, advantageously at least one additional reinforcing rib is provided, in addition to the two reinforcing ribs enclosing the heating wires, in or under which a control-signal line is conducted around the hose wall. Alternatively or additionally, it can be advantageous to conduct a measuring-signal line through at least one reinforcing rib. That means that, for example, three, four or more reinforcing ribs can be provided, forming together a helical line with three, four or more threads around or along the hose wall, two of the reinforcing ribs expediently enclosing one heating wire each, in the above-described manner, and each of the additional reinforcing ribs enclosing one of the additional wires provided for control or measuring purposes. Open-loop and/or closed-loop control lines as well as measuring-signal lines can be used, for example, for measuring and, if necessary, controlling the temperature of the hose and/or the fluid flowing therein, using suitable measuring probes.

The function or the assignment of the individual heating wires or electric conductors associated to the respective reinforcing ribs can be marked in a comfortable and easily recognizable manner by different colours of the reinforcing ribs.

The use of more than one helicoidal reinforcing rib allows further application-specific realization possibilities of the hose. This can be achieved in particular by making the individual reinforcing ribs of different materials, preferably of different synthetic materials. In this way, different mechanical properties of the hose can be realized. By using a material of high Shore hardness for one or more of the reinforcing spirals, for example, the radial strength of the hose can be increased. Furthermore, the abrasion behavior and/or the coefficients of friction can be influenced in an optimized manner through the selection of the materials for the individual reinforcing ribs. The materials may differ in hardness, abrasion resistance, surface smoothness or surface adhesion. In this way, characteristics which are typical of a hose, such as radial strength, minimum bend radius, abrasion resistance, and sliding behavior can be realized in a manner optimized for the specific application.

In addition to the variation of the material, a variation of the cross-sectional shape and/or the cross-sectional dimensions or, more generally, of the geometry of the reinforcing ribs may turn out to be advantageous, for example in order to optimize the the minimum bend radius of the hose.

The minimum bend radius of a hose is defined as the radius of the smallest drum around which the hose can be laid without the hose cross-section considerably changing its original shape. The bend radius depends among others on the inner diameter of the hose, the wall thickness and the materials used. If one or more reinforcing spirals are arranged outside the hose wall, the reinforcing spirals will touch each other, when the hose is strongly bent, in the area of the inner curvature. When bending the hose, the minimum bend radius of the hose will be reached at the latest when all reinforcing ribs touch each other in the area of the inner curvature. If, however, for example, one reinforcing spiral is designed with a laterally convex cross-section and a second reinforcing spiral, with a laterally concave cross-section, the two profiles can slide into one another inside the inner curvature, when the hose is strongly bent. This reduces the distance between the respective central points of the reinforcing spirals, as compared with an embodiment with two convex profiles, and the minimum bend radius can in this way be kept very small.

Furthermore, the cross-sectional profile of a helicoidal reinforcing rib can be designed in such a way that it protrudes, in a direction normal to the hose axis, over the other reinforcing ribs, i.e. in a side view of the hose, protrudes further over the hose wall than the other reinforcing ribs. If a hose designed in such a way lies, for example, on a rough, but substantially flat surface, the hose will have contact with the surface underneath it with this protruding reinforcing spiral only. In this way, the number of contact points of the hose with the surface underneath it can be reduced, thus reducing the risk of a catching of the hose on a surface. Variations of the geometric design of the reinforcing ribs can influence the properties of the hose not only concerning radial strength and bend radius, but can also provide additional possibilities of fastening end pieces on the hose.

In a preferred embodiment, the heating wires are connected with each other on one end of the hose in an electrically conductive manner. On the other end of the hose, the heating wires can be connected with the poles of a voltage source or a heating-current source. Thus, the entire hose can be heated in a simple manner, using only one voltage or current source. In an alternative embodiment, two voltage or current sources can be used, the heating wires being connected on both ends of the hose in each case with opposite poles of the voltage or current sources.

The wall of the hose is preferably formed of a self-overlapping plastic tape.

In another modification, for example, four reinforcing ribs can be provided, each of which encloses one heating wire and which form together a four-threaded helical line. Two heating wires each form a heating-current circuit. With this variant, a particularly high heating power can be realized.

The advantages achieved with the invention consist in particular in that the use of two helicoidal reinforcing ribs, each of which carrying only one single-conductor heating wire, can reliably avoid a contact of the two conductors and, therefore, a short circuit. If two or more reinforcing spirals are used, winding around the hose wall in the manner of a double or multiple helix, these can be made with a higher lead than in an embodiment with only one reinforcing spiral. This can, on the one hand, guarantee a high flexibility of the hose and, on the other hand, save material for the heating wires. The use of more than two reinforcing ribs allows to additionally carry control or measuring lines. Different embodiments of the respective reinforcing spirals with regard to their color, cross-section and material properties offer a multitude of parameters, through which the characteristics and handling of the hose for the application in question can be adapted in an optimized manner.

BRIEF DESCRIPTION OF THE DRAWINGS

An exemplary embodiment of the invention is discussed by means of a drawing, in which, in greatly schematic representations, FIG. 7 is a top view of the hose with two reinforcing ribs in an alternative embodiment, the two reinforcing ribs having different cross-sectional profiles.

DETAILED DESCRIPTION

Figure 1:
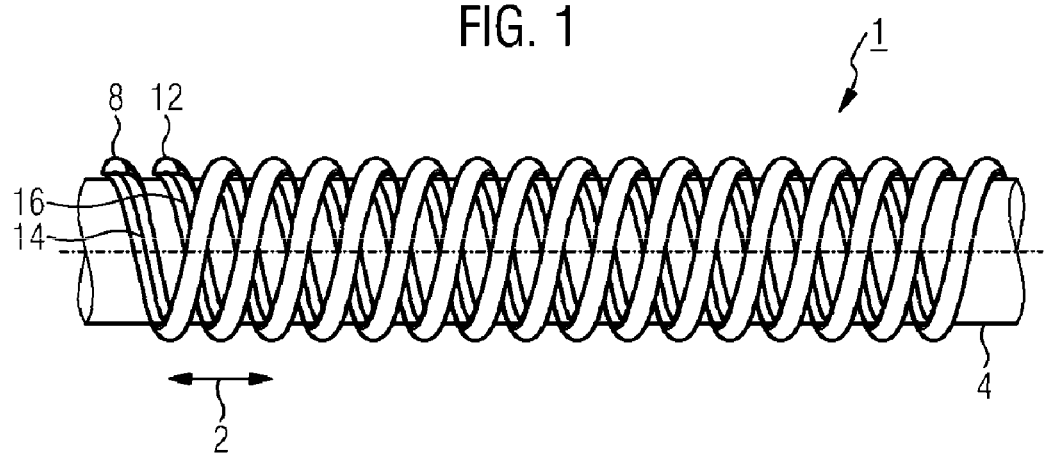
FIG. 1 is a side view of a heatable hose of a first embodiment with a hose wand and two helicoidal reinforcing ribs.

The heatable hose 1 shown in FIG. 1 is used in particular as a respiration hose. Viewed in longitudinal direction 2 of the hose, the hose wall 4 (transparent in this case) is surrounded by two helicoidal reinforcing ribs 8, 12. The two reinforcing ribs 8, 12 form together a two-threaded helical line or double helix. The reinforcing rib 8 surrounds or encloses a first single-conductor heating wire 14 with a suitably selected resistivity, and the reinforcing rib 12 encloses a second single-conductor heating wire 16, preferably having the same electric and mechanical characteristics as the first heating wire 14. The heating wires 14, 16 are connected with each other on one end of the hose 1 in an electrically conductive manner and are led out of the respective reinforcing rib 8, 12 on the other end of the hose 1. To heat the hose 1, the connection pieces of the heating wires 14, 16 led out of the reinforcing ribs 8, 12 are connected with the poles of a voltage source or heating-current source.

The separate carrying of only one single-conductor heating wire in one reinforcing spiral each results in a material and spatial isolation of the two heating wires. Thus, the risk of a short circuit can completely be avoided or greatly reduced. The hose wall 4 preferably consists of a self-overlapping plastic tape. The overlapping region may form in particular a connection point to the respective reinforcing rib or spiral.

The reinforcing ribs can be made, for example, of a synthetic material, which guarantees electric insulation of the embedded heating wire against the environment. Therefore, the respective heating wire does not require a separate cleading of its own.

Figure 2:
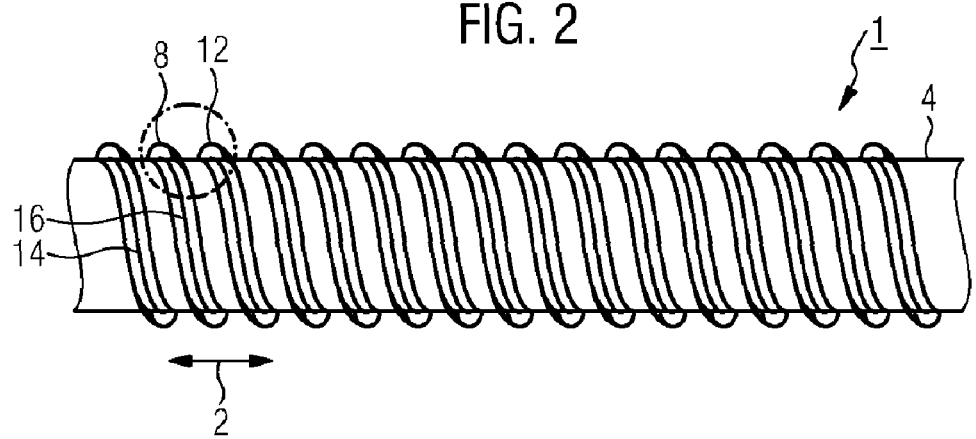
FIG. 2 is a longitudinal section through the hose of FIG. 1.
Figure 3:
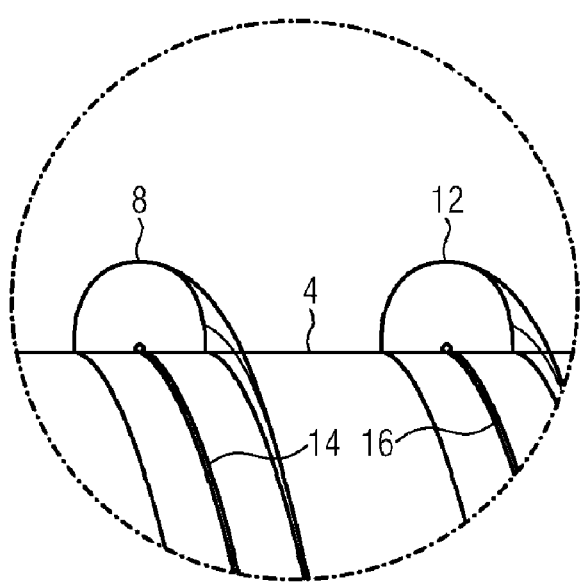
FIG. 3 is an enlarged detail of the circle marked in FIG. 2.

FIG. 2 shows a lateral section through the hose 1 represented in FIG. 1. The course of the heating wires zwischen hose wall 4 and reinforcing ribs 8, 12 is particularly well recognizable in this representation. FIG. 3 shows an enlarged detail of a section through the reinforcing ribs 8, 12 at the upper end of the hose wall 4. The reinforcing rib 8 encloses the heating wire 14, the reinforcing rib 12 encloses the heating wire 16. In the shown embodiment, a small channel accommodating the respective heating wire 14, 16 is formed in each reinforcing rib 8, 12, so that the heating wires 14, 16 are enclosed by the reinforcing ribs 8, 12 and the hose wall 4.

Figure 4:
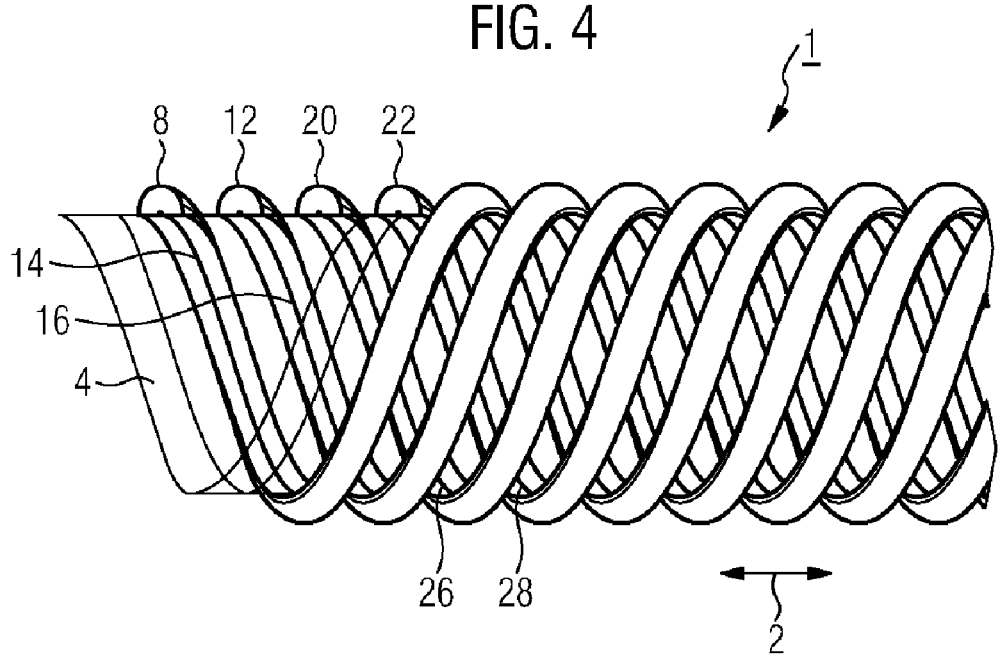
FIG. 4 is a side view of the hose of a second embodiment with four helicoidal reinforcing ribs.

FIG. 4 shows another preferred embodiment of the hose 1. The hose 1 includes four reinforcing ribs 8, 12, 20, 22. The ribs 8, 12 accommodate the heating wires 14, 16. The reinforcing rib 20 accommodates a measuring line 26, the reinforcing rib 22 accommodates an open-loop control line 28 or a closed-loop control line. Through the use of a temperature probe integrated in the hose 1 or fixed on the hose 1, and with the help of an external control device, the heating of the hose 1 can be controlled. As a function of the difference between nominal and actual value of the temperature, the heating current led through the heating wires can be increased or decreased, until the desired temperature is reached. The different reinforcing ribs 8, 12, 20, 22 are marked, depending on their function, with different colors. The color marking of the reinforcing ribs 8, 12, 20, 22 greatly simplifies the installation of a hose 1 and the expedient connection of the lines embedded in the reinforcing ribs 8, 12, 20, 22 with the voltage source and/or the respective terminals.

Figure 5:
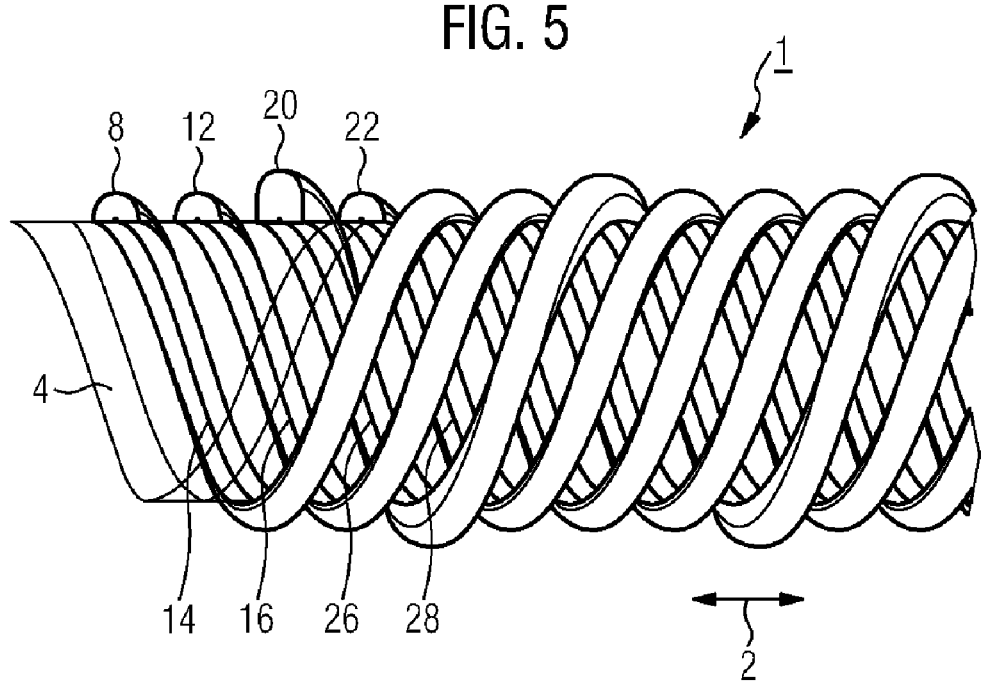
FIG. 5 is a side view of the hose of another embodiment with one reinforcing rib protruding laterally over the other reinforcing ribs.

FIG. 5 shows another preferred embodiment of the hose 1. The hose 1 includes four reinforcing ribs 8, 12, 20, 22. The reinforcing ribs 8, 12, 22 have identical cross-sectional profiles. The reinforcing rib 20 protrudes laterally, i.e. it extends farther outwards, radially to the hose axis, than the other reinforcing ribs 8, 12 and 22. A support surface (not shown here), on which the hose 1 rests, has contact with the latter substantially only by the reinforcing rib 20. This can reduce the risk of a catching of the hose on the surface underneath it, but also on other obstacles or objects.

Figure 6:
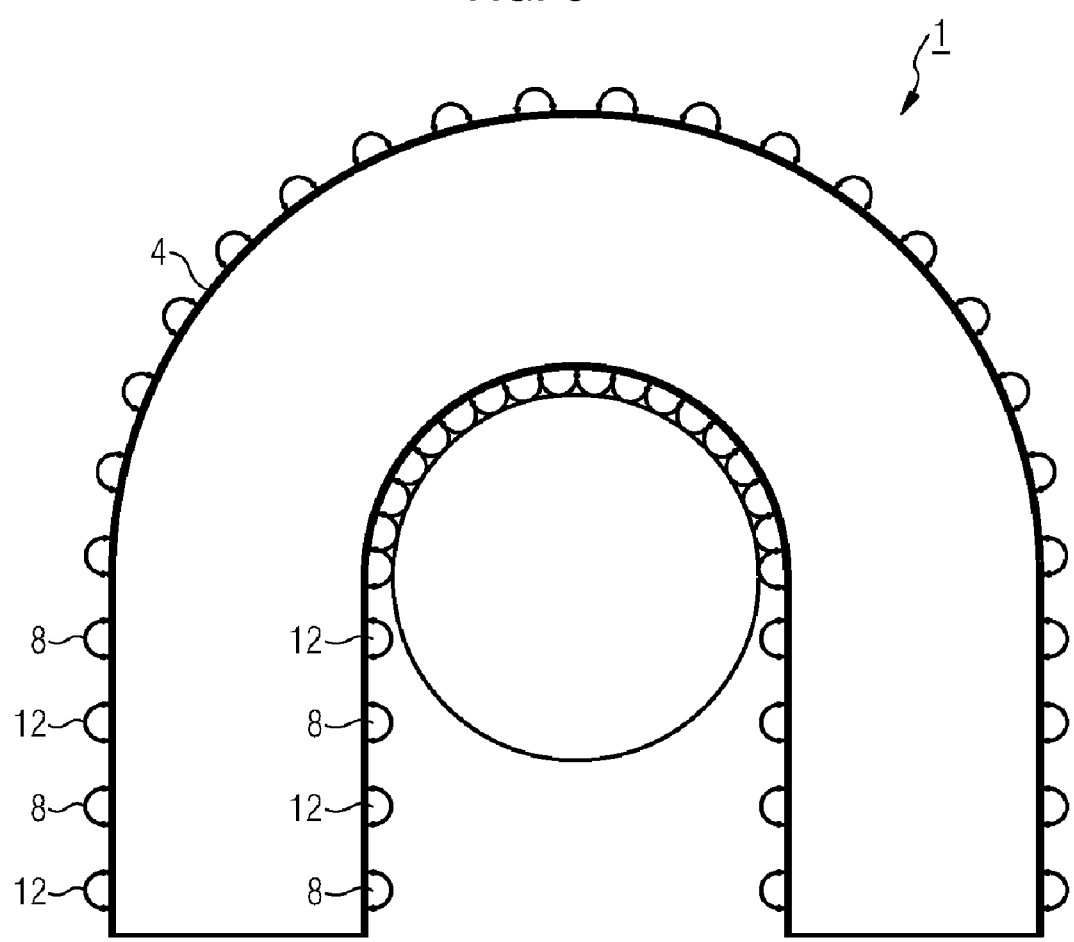
FIG. 6 is a top view of the hose of FIG. 1, bent in one place by 180 degrees, the two reinforcing ribs having cross-sectional profiles of the same design.

The embodiment of the hose 1 shown in FIG. 6 includes two helicoidal reinforcing ribs 8 and 12, having identical cross-sectional profiles. The hose 1 shown in the figure is bent by 180°, whereby the minimum bend radius has been realized. The minimum bend radius of a hose 1 is characterized by the fact that upon corresponding bending, its cross-sectional profile just remains substantially unchanged. In the inner curvature of the bend, the reinforcing ribs 8 and 12 are in lateral contact with each other. The reinforcing ribs 8, 12, which are in contact with each other, prevent in this way an even stronger bending of the hose 1.

FIG. 7 shows an alternative embodiment of the hose 1 with two reinforcing ribs 8, 12. Here, too, the hose 1 is bent by 180°, whereby in this example, too, the minimum bend radius has been realized. Sizing and dimensions of the hose wall 4 and the reinforcing rib 8 of the hoses shown in FIG. 6 and FIG. 7 are identical. This embodiment of the hose 1 also includes two helicoidal reinforcing ribs, which, however, in this case are designed with different cross-sectional profiles. While the profile of the reinforcing rib 8 is semicircular and, therefore, convex, the profile of the reinforcing rib 12 includes lateral indentations. Due to its concave design, the reinforcing rib 12 can partially accommodate the reinforcing rib 8 on the sides in the inner curvature. By fitting the reinforcing-rib profiles into each other in this way on the inner curvature radius, a narrower spatial arrangement of the reinforcing ribs 8, 12 can be achieved. Through this measure, the minimum bend radius of the hose 1 shown in FIG. 7 is approx. 8% smaller than the minimum bend radius of the hose 1 shown in FIG. 6.

If more than two reinforcing ribs 8, 12 are used, a minimum bend radius suitable for the application in question can, in this case, too, be realized by an optimized selection of the cross-sectional profiles of the various reinforcing ribs 8, 12, 20, 22. Additionally, the materials of the reinforcing ribs 8, 12, 20, 22 may differ, so that properties of the hose, such as radial strength, abrasion resistance and sliding behavior of the hose on a surface can be influenced. The materials may differ in properties such as hardness, abrasion resistance and surface smoothness or surface adhesion. Furthermore, for example, different synthetic materials can be used.

LIST OF REFERENCE NUMBERS

| | |
|---|---|
| 1 | Hose |
| 2 | Longitudinal direction |
| 4 | Hose wall |
| 8, 12, 20, 22 | Reinforcing ribs |
| 14, 16 | Heating wire |
| 26 | Measuring-signal line |
| 28 | Control-signal line |

What is claimed is:

1. A heatable hose (1) comprising:
a flexible hose wall (4);
a plurality of reinforcing ribs (8, 12, 20, 22), each of which winds around the hose wall (4) in the manner of a helical line and which form together a multiple-threaded helical line, at least two reinforcing ribs (8, 12) being provided, each of which encloses a heating wire (14, 16) designed for heating the hose (1);
wherein the reinforcing ribs (8, 12, 20, 22) have different cross-sectional shapes and/or cross-sectional dimensions; and
wherein exactly one reinforcing rib (8, 12, 20, 22) protrudes over the other reinforcing ribs (8, 12, 20, 22) in a direction normal to the hose axis.

2. The hose (1) according to claim 1, wherein the respective heating wire (14, 16) is a single-conductor wire.

3. The hose (1) according to claim 1, having exactly two reinforcing ribs (8, 12), which form together a double-threaded helical line.

4. The hose (1) according to claim 1, having at least three reinforcing ribs (8, 12, 20, 22), at least one of the reinforcing ribs (8, 12, 20, 22) enclosing a control-signal line (28).

5. The hose (1) according to claim 1, having at least three or four ribs (8, 12, 20, 22), at least one of the reinforcing ribs (8, 12, 20, 22) enclosing a measuring-signal line (26).

6. The hose (1) according to claim 1, wherein the reinforcing ribs (8, 12, 20, 22) are designed in different colors.

7. The hose (1) according to claim 1, wherein the reinforcing ribs (8, 12, 20, 22) consist of different materials.

8. The hose (1) according to claim 1, wherein the heating wires (14, 16) are connected with each other on one end of the hose (1) in an electrically conductive manner.

9. The hose (1) according to claim 1, wherein the hose wall (4) is formed of a self-overlapping plastic tape.

10. The hose (1) according to claim 1, wherein the heatable hose is a respiration hose.

11. A heatable hose comprising a hose wall that is flexible, and at least two reinforcing ribs each winding in a helical line around the hose wall that together form a multiple threaded helical line, with at least one of the ribs enclosing a heating wire for heating the hose, with at least two of the ribs having different cross-sectional shapes and/or dimensions, and with exactly one of the ribs protruding over the other ribs in a direction normal to the hose axis.

12. The hose of claim 11 wherein a self-overlapping plastic tape forms the hose wall.

13. The hose of claim 11 wherein two of the ribs carry heating wires that are electrically connected at one end of the hose.

14. The hose of claim 11 wherein at least one of the ribs carries a single conductor wire.

15. The hose of claim 11 wherein the ribs are at least three in number.

16. The hose of claim 11 wherein at least one of the ribs encloses a measuring-signal line.

17. The hose of claim 11 wherein at least one of the ribs consists of a different material than forms at least one other of the ribs.

18. The hose of claim 11 wherein at least one of the ribs exhibits a different color that does at least one other of the ribs.

19. The hose of claim 11 wherein all of the ribs carry a wire that is a heating wire for heating the hose.

* * * * *